United States Patent [19]

Kraatz et al.

[11] Patent Number: 4,465,680
[45] Date of Patent: Aug. 14, 1984

[54] COMBATING FUNGI WITH AZOLYLVINYLDITHIOACETALS

[75] Inventors: Udo Kraatz; Gerhard Jäger, both of Leverkusen; Karl H. Büchel, Burscheid; Paul-Ernst Frohberger, Leverkusen, all of Fed. Rep. of Germany

[73] Assignee: Bayer Aktiengesellschaft, Leverkusen, Fed. Rep. of Germany

[21] Appl. No.: 438,061

[22] Filed: Nov. 1, 1982

[30] Foreign Application Priority Data

Nov. 19, 1981 [DE] Fed. Rep. of Germany ....... 3145890

[51] Int. Cl.³ .................... A01N 43/50; A01N 43/64; C07D 249/08; C07D 233/60
[52] U.S. Cl. .................... 424/245; 424/184; 424/269; 424/273 R; 424/232; 548/101; 548/110; 548/262; 548/336; 548/341
[58] Field of Search ............... 548/101, 110, 262, 341, 548/336; 424/245, 232, 269, 273 R, 184

[56] References Cited

FOREIGN PATENT DOCUMENTS 0001928 5/1979 European Pat. Off. .
0040368 11/1981 European Pat. Off. .

Primary Examiner—Alton D. Rollins
Attorney, Agent, or Firm—Sprung, Horn, Kramer & Woods

[57] ABSTRACT

New azolylvinyldithioacetals of the formula

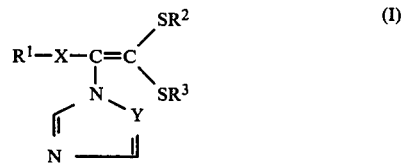

in which
$R^1$ is an alkyl, optionally substituted cycloalky, optionally substituted phenyl or alkoxy group,
$R^2$ and $R^3$ are identical and each is an alkyl, alkenyl, alkinyl, optionally substituted benzyl or trialkylsilyl group,
$R^2$ and $R^3$ together form an alkylene chain, a dialkylsilyl bridge or a —CH=CH— group,
X is a keto group or a CH—(OH) group, and
Y is a nitrogen atom or a CH group, and their acid addition salts and metal salt complexes are prepared as described and find use as fungicides.

10 Claims, No Drawings

COMBATING FUNGI WITH AZOLYLVINYLDITHIOACETALS

The present invention relates to certain new azolyl-vinyldithioacetals, to a process for their production, and to their use as fungicides.

It has already been disclosed that certain triazolylalkenones and triazolylalkenols possess good fungicidal properties (see U.S. Pat. No. 4,331,675). Thus, for example, 4,4-dimethyl-1-(naphth-2-yl)-2-(1,2,4-triazol-1-yl)-pent-1-en-3-one and 4,4-dimethyl-1-(naphth-2-yl)-2-(1,2,4-triazol-1-yl)-pent-1-en-3-ol can be employed for combating fungi. However, the action of these compounds is not always very satisfactory, particularly when low amounts and concentrations are used.

The present invention now provides, as new compounds, the azolylvinyldithioacetals of the general formula

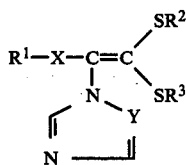

in which

R$^1$ represents an alkyl, optionally substituted cycloalkyl, optionally substituted phenyl or alkoxy group, R$^2$ and R$^3$ are identical and each represent an alkyl, alkenyl, alkinyl, optionally substituted benzyl or trialkylsilyl group, or R$^2$ and R$^3$ together represent an alkylene chain, a dialkylsilyl bridge or a —CH=CH group, X represents a keto group or a CH—(OH) group, and Y represents a nitrogen atom or a CH group, and acid addition salts and metal salt complexes thereof.

According to the present invention we further provide a process for the production of a compound of the present invention, characterized in that carbon disulphide is first added to an α-azolyl-ketone of the general formula

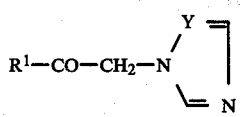

in which R$^1$ and Y have the meanings given above, in the presence of a base and in the presence of a diluent, given above, in the presence of a base and in the presence of a diluent, and the product is then reacted either (α) with a compound of the general formula

   (III)

in which

Hal represents a halogen atom and

R$^4$ represents an alkyl, alkenyl, alkinyl, optionally substituted benzyl or trialkylsilyl group, or (β) with dimethyl sulphate of the formula (CH$_3$)$_2$SO$_4$   (IV)

or (γ) with a dihalide of the general formula

Hal'—R$^5$—Hal'   (V)

in which

Hal' represents a halogen atom and

R$^5$ represents a one-membered or multi-membered methylene chain, a dialkylsilyl bridge or a —CH=CH— group, in the presence of the same diluent;

and, if a compound of formula (I) is required in which X denotes a CH—(OH) group, the resulting keto derivative of the general formula

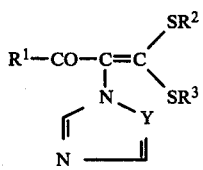

in which

R$^1$, R$^2$, R$^3$ and Y have the meanings given above, is reduced;

and, if desired, an acid or a metal salt is then added onto the resulting compound of the formula (I).

Finally, it has been found that the new azolylvinyldithioacetals of the formula (I), and their acid addition salts and metal salt complexes, possess powerful fungicidal properties.

Surprisingly, the substances according to the invention exhibit a better fungicidal activity than the compounds 4,4-dimethyl-1-(naphth-2-yl)-2-(1,2,4-triazol-1-yl)-pent-1-en-3-one and 4,4-dimethyl-1-(naphth-2-yl)-2-(1,2,4-triazol-1-yl)-pent-1-en-3-ol, which are known from the prior art and are similar compounds with respect to their action.

Preferred azolylvinyldithioacetals according to the present invention are those in which, R$^1$ represents a straight-chain or branched alkyl group having 1 to 4 carbon atoms or a cycloalkyl group which has 3 to 7 carbon atoms and is optionally substituted by alkyl having 1 to 4 carbon atoms, or represents a straight-chain or branched alkoxy group having 1 to 4 carbon atoms or an optionally substituted phenyl group, the substituent(s) thereon being selected from halogen, alkyl, alkoxy and alkylthio, each having 1 to 4 carbon atoms, halogenoalkyl, halogenoalkoxy and halogenoalkylthio, each having 1 to 2 carbon atoms and up to 5 identical or different halogen atoms (such as especially fluorine atoms and chlorine atoms), and phenoxy and phenyl optionally substituted by halogen and/or by alkyl having 1 or 2 carbon atoms;

R$^2$ and R$^3$ represent the same radical which is a straight-chain or branched alkyl group having 1 to 4 carbon atoms; a straight-chain or branched alkenyl or alkinyl group, each having 2 to 6 carbon atoms; an optionally substituted benzyl group, the substituent(s) in the phenyl ring of the benzyl group being selected from halogen, alkyl, alkoxy and alkylthio, each having 1 to 4 carbon atoms, halogenoalkyl, halogenoalkoxy and halogenoalkylthio, each having 1 or 2 carbon atoms and up to 5 identical or different halogen atoms (such as, especially fluorine atoms and chlorine atoms), and phenoxy and phenyl optionally substituted by halogen and/or by alkyl having 1 or 2 carbon atoms; or represent a trialkylsilyl group having 1 to 4 carbon atoms in each alkyl part; or R² and R³ together represent an alkylene chain having 1 to 4 carbon atoms, a dialkylsilyl bridge having 1 to 4 carbon atoms in each alkyl part, or a —CH=CH— group, X represents the keto group or a CH(OH) group, and
Y represents a nitrogen atom or a CH group.

Particularly preferred compounds of the present invention are those in which

R¹ represents a tert.-butyl or isopropyl group, a cyclopropyl, cyclopentyl or cyclohexyl group which is optionally substituted by methyl, ethyl or propyl, a methoxy, ethoxy or butoxy group, an optionally substituted phenyl group, the substituent(s) being selected from fluorine, chlorine, methyl, isopropyl, tert.-butyl, methoxy, methylthio, isopropoxy, trifluoromethyl, trifluoromethoxy, trifluoromethylthio, and phenoxy or phenyl which is optionally substituted by fluorine, chlorine and/or methyl;

R² and R³ are identical and each represents a straight-chain or branched alkyl group having 1 to 4 carbon atoms, an allyl or propargyl group or an optionally substituted benzyl group, the substituent(s) in the phenyl ring of the benzyl group being selected from fluorine, chlorine, methyl, isopropyl, tert.-butyl, methoxy, methylthio, isopropoxy, trifluoromethyl, trifluoromethoxy, trifluoromethylthio, and phenoxy or phenyl which is optionally substituted by fluorine, chlorine and/or methyl, or R² and R³ are identical and represent a trimethylsilyl group, or R² and R³ together represent a methylene radical, a dimethylene or trimethylene chain, a dimethylsilyl bridge or a —CH=CH— group, X represents a keto group or a —CH(OH) group, and
Y represents a nitrogen atom or a CH group.

Addition products of acids and those azolylvinyldithioacetals of the formula (I), in which the substituents R¹, R², R³, X and Y have the meanings which have already been there mentioned, are included in the preferred and particularly preferred compounds according to the invention.

The acids which may be used to form adducts preferably include hydrohalic acids (such as hydrobromic acid, and, especially, hydrochloric acid), phosphoric acid, nitric acid, sulphuric acid, monofunctional and bifunctional carboxylic acids and hydroxycarboxylic acids (such as acetic acid, maleic acid, succinic acid, fumaric acid, tartaric acid, salicylic acid, sorbic acid and lactic acid) and sulphonic acids (such as p-toluene-sulphonic acid and naphthalene-1,5-disulphonic acid).

Likewise addition products of salts of metals of main groups II to IV and of sub-groups I and II and IV to VIII with those azolylvinyldithioacetals of the formula (I), in which the substituents R¹, R², R³, X and Y have the meanings which have already been there mentioned, are included in the preferred and particularly preferred compounds according to the invention. Amongst these, salts of copper, zinc, manganese, magnesium, tin, iron and nickel are particularly preferred. Suitable anions of these salts are those which are derived from those acids which lead to physiologically tolerated addition products. Particularly preferred acids of this type in this connection are hydrohalic acid (such as hydrochloric acid and hydrobromic acid), phosphoric acid, nitric acid and sulphuric acid.

If, for example, 1,2,4-triazolyl-pinacolin, carbon disulphide and dimethyl sulphate are used as starting materials, the course of the reaction in the process according to the invention can be represented by the following equation:

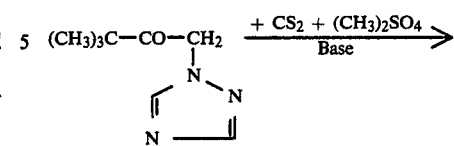

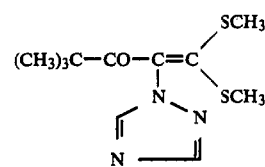

If, for example, 1,2,4-triazolyl-pinacolin, carbon disulphide and 1,2-dibromoethane are used as starting materials, the course of the reaction in the process according to the invention can be represented by the following equation:

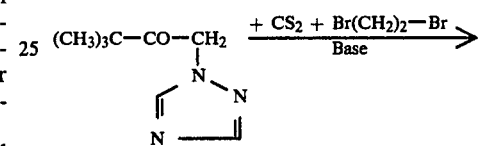

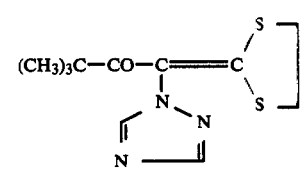

If, for example, 2,2-dimethyl-5,5-dimethylthio-4-(1,2,4-triazol-1-yl)-pent-4-en-3-one is used as the starting material and sodium borohydride is used as the reducing agent, the course of the reaction in the reduction according to the invention can be represented by the following equation:

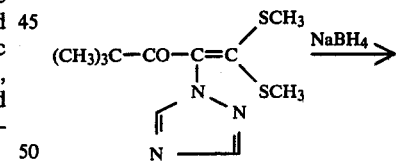

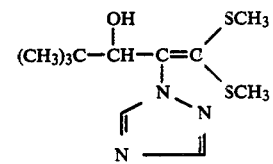

Preferred azolyl-ketones of formula (II) required as starting mateials in carrying out the process according to the invention are those in which R¹ and Y have the meanings which have already been mentioned for these radicals in the description of the preferred and particularly preferred compounds according to the invention.

α-Azolyl-ketones of the formula (II) are known, see U.S. Ser. Nos. 792,756, filed May 2, 1977 and 291,700, filed Aug. 10, 1981, both now pending and (see, for example DE-OS (German Published Specifications)

Nos. 2,638,470 and 3,010,560 and JACS 77, 621 (1955)), and can be obtained in a generally known manner by reacting the corresponding α-bromo (chloro)-ketones with imidazole or 1,2,4-triazole in the presence of an inert organic solvent (such as acetone) and in the presence of an acid-binding agent (such as potassium carbonate), preferably at the boil.

Preferred compounds of formula (III) and (V) additionally to be used as reactants for the process according to the invention are those in which, in the case of compounds of formula (VI), Hal represents a chlorine or bromine atom, and $R^4$ has the meanings which have already been mentioned for radical $R^2$ in the description of preferred and particularly preferred compounds according to the invention, and, in the case of compounds of formula (V) Hal' represents a chlorine or bromine atom, and $R^5$ has the meanings which have already been mentioned for substituents formed by $R^2$ and $R^3$ together, in the description of preferred and particularly preferred compounds according to the invention.

The compounds of the formulae (III), (IV) and (V) are generally known compounds of organic chemistry.

Suitable diluents for the process, according to the invention, for the preparation of keto derivatives of the formula (Ia) are organic solvents which are inert under the reaction conditions. These include, as preferences, ethers (such as tetrahydrofuran or dioxane), alcohols (such as methanol, ethanol or isopropanol), amides (such as dimethylformamide or dimethylacetamide), and also dimethylsulphoxide, hexamethylphosphoric acid triamide or sulpholane (tetrahydrothiophene-1,1-dioxide).

The process, according to the invention, for the preparation of the keto derivatives of the formula (Ia) is carried out in the presence of a base. These include, as preferences, alkali metal hydroxides and alcoholates (such as sodium and potassium hydroxide or sodium and potassium methylate, ethylate and tert.-butylate) and alkali metal hydrides and amides (such as sodium hydride, sodium amide or lithium isopropylamide, and butyl-lithium).

In carrying out the process, according to the invention, for the preparation of the keto derivatives of the formula (Ia), the reaction temperatures can be varied within a relatively wide range. In general, the reaction is carried out at a temperature between 0° and 80° C., preferably between 0° and 60° C.

In carrying out the process, according to the invention, for the preparation of the keto derivatives of the formula (Ia), 1 to 1.1 mols of carbon disulphide and 2 mols of base and 2 mols of a compound of the formula (III) or (IV), or 1 mol of a compound of the formula (V), are preferably employed per mol of α-azolyl-ketone of the formula (III). Preferably, in this process, the ketone of the formula (II) is initially introduced, first half the amount of carbon disulphide and base is added, then the remaining amount of carbon disulphide and base is added, and finally the particular reactant of the formula (III), (IV) or (V) is added. The isolation of the compounds of the formula (Ia) is effected in the customary manner.

If complex hydrides are used, suitable diluents for the reduction, according to the invention, of the keto derivatives of the formula (Ia) are polar organic solvents. These preferably include alcohols (such as methanol, ethanol, butanol and isopropanol) and ethers (such as diethyl ether or tetrahydofuran). This reaction is carried out in general at a temperature between 0° and 30° C., preferably between 0° and 20° C. For this purpose, about 1 reaction equivalent of a complex hydride, such as sodium borohydride or lithium alanate, is employed per mol of a ketone of the formula (Ia). To isolate the reduced compounds of the formula (I), the residue is taken up in dilute hydrochloric acid, and the solution is then rendered alkaline and extracted with an organic solvent. Further working-up is effected in the customary manner.

If aluminum isopropylate is used in the reduction of the keto derivatives of the formula (Ia), preferred diluents for the reaction according to the invention are alcohols (such as isopropanol) or inert hydrocarbons (such as benzene). In this case also, the reaction temperatures can be varied within a relatively wide range. In general, the reaction is carried out at a temperature between 20° and 120° C., preferably between 50° and 100° C. To carry out the reaction, about 1 to 2 mols of aluminum isopropylate are employed per mol of a ketone of the formula (Ia). To isolate the reduced compounds of the formula (I), the excess solvent is removed by distillation in vacuo, and the aluminum compound formed is decomposed with dilute sulphuric acid or sodium hydroxide solution. Further working-up is effected in the customary manner.

Preferred acids for the preparation of acid addition salts of the compounds of the formula (I) are those which have already been mentioned in connection with the description of the acid addition salts according to the invention as being preferred acids.

The acid addition salts of the compounds of the formula (I) can be obtained in a simple manner by customary methods of salt formation, for example by dissolving a compound of the formula (I) in a suitable inert solvent and adding the acid (for example hydrochloric acid), and can be isolated in a known manner, for example by filtration, and if appropriate purified by washing with an inert organic solvent.

Preferred salts for the preparation of metal salt complexes of compounds of the formula (I) are the salts of those anions and cations which have already been mentioned in connection with the description of the metal salt complexes according to the invention as being preferred.

The metal salt complexes of compounds of the formula (I) can be obtained in a simple manner by customary processes, thus, for example, by dissolving the metal salt in an alcohol (for example ethanol) and adding the solution to the compound of the formula (I). Metal salt complexes can be isolated in a known manner, for example by filtration, and if appropriate purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating those fungi which cause powdery mildew diseases, thus, for combating Erysiphe species, such as, for example, against the powdery mildew of barley or cereals causative organism (*Erysiphe graminis*), for combating Venturia species, such as, for example, against the apple scab causative organism (*Venturia inaequalis*), or for combating rice diseases, such as, for example, *Pellicularia sasakii*.

It should be emphasized that the substances according to the invention also have good bactericidal properties.

The active compounds can be converted to the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions for seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are generally required at the place of action.

The preparation and the use of the active compounds according to the invention are illustrated by the examples which follow.

PREPARATIVE EXAMPLES

Example 1

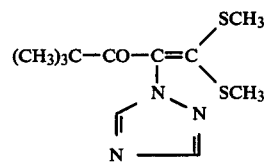

4 g (0.1 mol) of sodium hydroxide powder were added to 16 g (0.1 mol) of 1,2,4-triazolyl-pinacolin in 1,000 ml of dimethylsulphoxide. 4 g (0.053 mol) of carbon disulphide were added dropwise to the mixture while stirring at room temperature. Thereafter, 4 g (0.1 mol) of sodium hydroxide powder and 4 g (0.053 mol) of carbon disulphide were again added to the reaction mixture. The mixture was stirred for a further 20 minutes at room temperature. Thereafter, 25.3 g (0.2 mol) of dimethyl sulphate were slowly added dropwise while cooling with ice, the internal temperature being kept at approximately 30° C. After the reaction mixture had been stirred for 3 hours at room temperature, it was poured into water and extracted with methylene chloride. The organic phase was dried and concentrated, and the residue was chromatographed over a silica gel column, using a chloroform/ethyl acetate eluant. 2,2-Dimethyl-5,5-dimethylthio-4-(1,2,4-triazol-1-yl)-pent-4-en-3-one of melting point 60° C. were obtained in a yield of 53%.

Example 2

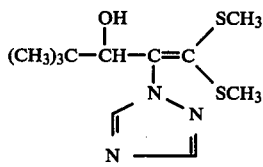

15 g (0.055 mol) of 2,2-dimethyl-5,5-dimethylthio-4-(1,2,4-triazol-1-yl)-pent-4-en-3-one (obtained as described in Example 1) were dissolved in 100 ml of methanol, and 2.1 g (0.055 mol) of sodium borohydride were added at room temperature. The mixture was stirred for a further 30 minutes at 20° to 30° C., and was concentrated. The residue was partitioned between methylene chloride and water. The organic phase was separated off, dried over sodium sulphate and concentrated. 11.9 g (80% of theory) of 2,2-dimethyl-5,5-dimethylthio-4-(1,2,4-triazol-1-yl)-pent-4-en-3-ol of melting point 108° to 111° C. were obtained.

Example 3

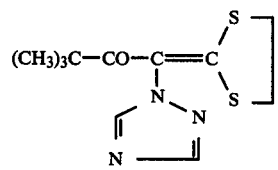

4 g (0.1 mol) of sodium hydroxide powder were added to 16 g (0.1 mol) of 1,2,4-triazolyl-pinacolin in 100 ml of dimethylsulphoxide. 4 g (0.053 mol) of carbon disulphide were added dropwise to the mixture while stirring at room temperature. Thereafter, 4 g (0.1 mol) of sodium hydroxide powder and 4 g (0.053 mol) of carbon disulphide were again added to the reaction mixture. The mixture was stirred for a further 20 minutes at room temperature. Thereafter, 18.8 g (0.1 mol) of 1,2-dibromoethane were added dropwise, while cooling with ice, at such a rate that the internal temperature did not exceed 30° C. After the reaction mixture had been stirred for 3 hours at room temperature, it was poured into water. The precipitated product was filtered off under suction and recrystallized from isopropanol. 14.2 g (53% of theory) of 3,3-dimethyl-1-(1,3-dithiolan-2-ylidene)-1-(1,2,4-triazol-1-yl)-butan-2-one of melting point 141° C. were obtained.

The compounds of the formula (I) which are listed in Table 1 below were obtained in an analogous manner and according to the process according to the invention.

TABLE 1

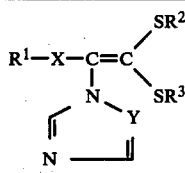

(I)

| Compound No. | $R^1$ | X | Y | $R^2$ | $R^3$ | Boiling point (b.p.) or melting point (°C.)/ or refractive index ($n_D^{20}$) |
|---|---|---|---|---|---|---|
| 4 | $(CH_3)_3C-$ | CO | N | $-CH_2-\langle\bigcirc\rangle-Cl$ | $-CH_2-\langle\bigcirc\rangle-Cl$ | 114 |
| 5 | $(CH_3)_3C-$ | CO | N | $-CH_2-C\equiv CH$ | $-CH_2-C\equiv CH$ | viscous oil |
| 6 | $(CH_3)_3C-$ | CO | N | $-CH_2-CH=CH_2$ | $-CH_2-CH=CH_2$ | $n_D^{20} = 1.5611$ |
| 7 | $(CH_3)_3C-$ | CO | N | $-CH_2-\langle\bigcirc\rangle$ | $-CH_2-\langle\bigcirc\rangle$ | 81 |
| 8 | $(CH_3)_3C-$ | CO | N | $-CH_2-\langle\bigcirc\rangle$ Cl | $-CH_2-\langle\bigcirc\rangle$ Cl | 93 |
| 9 | $\langle\bigcirc\bigcirc\rangle$ | CO | N | $-CH_2-CH_2-$ | | 185 |
| | | CO | N | | $CH_{\not{p}}$ | $n_D^{20} = 1.6372$ |

TABLE 1-continued $$R^1-X-C=C\begin{smallmatrix}SR^2\\SR^3\end{smallmatrix} \quad (I)$$

with N—Y ring containing N=

| Compound No. | $R^1$ | X | Y | $R^2$ | $R^3$ | Boiling point (b.p.) or melting point (°C.)/ or refractive index ($n_D^{20}$) |
|---|---|---|---|---|---|---|
| 11 | Cl—C$_6$H$_4$— | CO | N | —CH$_2$—CH$_2$— | | 187 |
| 12 | Cl—C$_6$H$_4$— | CO | N | —CH$_2$—C$_6$H$_4$—Cl | —CH$_2$—C$_6$H$_4$—Cl | 112 |
| 13 | Cl—C$_6$H$_4$— | CO | N | —CH$_2$—C≡CH | —CH$_2$—C≡CH | viscous oil |
| 14 | Cl—C$_6$H$_4$— | CO | N | —CH(CH$_3$)$_2$ | —CH(CH$_3$)$_2$ | 113 |
| 15 | (CH$_3$)$_3$C— | CO | N | —CH(CH$_3$)$_2$ | —CH(CH$_3$)$_2$ | 75–78 |
| 16 | (CH$_3$)$_3$C— | CO | N | —CH$_2$— | | 134 |
| 17 | Cl—C$_6$H$_4$— | CO | N | —CH$_2$— | | 174 |
| 18 | C$_2$H$_5$O— | CO | N | —CH$_2$— | | 114–15 |
| 19 | C$_2$H$_5$O— | CO | N | —CH$_2$—C$_6$H$_4$—Cl | —CH$_2$—C$_6$H$_4$—Cl | 75 |
| 20 | C$_2$H$_5$O— | CO | N | —CH$_3$ | —CH$_3$ | 68–70 |
| 21 | C$_2$H$_5$O— | CO | N | —CH$_2$—CH=CH$_2$ | —CH$_2$—CH=CH$_2$ | $n_D^{20}$ = 1.5570 |
| 22 | C$_2$H$_5$O— | CO | N | —CH(CH$_3$)$_2$ | —CH(CH$_3$)$_2$ | b.p. 140° C./ 0.1 mm Hg |
| 23 | (CH$_3$)$_3$C— | CH(OH) | N | —CH$_2$—CH$_2$— | | 168 |
| 24 | (CH$_3$)$_3$C— | CH(OH) | N | —CH$_2$—C$_6$H$_4$—Cl | —CH$_2$—C$_6$H$_4$—Cl | 155 |
| 25 | (CH$_3$)$_3$C— | CH(OH) | N | —CH(CH$_3$)$_2$ | —CH(CH$_3$)$_2$ | 58 |
| 26 | Cl—C$_6$H$_4$— | CH(OH) | N | —CH$_2$—C$_6$H$_4$—Cl | —CH$_2$—C$_6$H$_4$—Cl | 139–41 |
| 27 | Cl—C$_6$H$_4$— | CH(OH) | N | —CH$_2$—CH$_2$— | | 158 |
| 28 | (CH$_3$)$_3$C— | CH(OH) | N | —CH$_2$—CH=CH$_2$ | —CH$_2$—CH=CH$_2$ | $n_D^{20}$ = 1.5428 |
| 29 | C$_6$H$_5$ | CH(OH) | N | —CH$_2$—CH$_2$— | | 133 |
| 30 | C$_6$H$_5$ | CH(OH) | N | —CH$_3$ | —CH$_3$ | 121 |
| 31 | (CH$_3$)$_3$C— | CH(OH) | N | —CH$_2$—C$_6$H$_5$ | —CH$_2$—C$_6$H$_5$ | 142 |
| 32 | (CH$_3$)$_3$C— | CH(OH) | N | —CH$_2$— | | 120 |
| 33 | (CH$_3$)$_3$C— | CH(OH) | CH | —CH$_3$ | —CH$_3$ | 43–47 |
| 34 | (CH$_3$)$_3$C— | CO | CH | —CH$_2$—C$_6$H$_4$—Cl | —CH$_2$—C$_6$H$_4$—Cl | 94 |

TABLE 1-continued $$R^1-X-C=C\begin{smallmatrix}SR^2\\SR^3\end{smallmatrix}$$ (I)
(with the N-Y-N ring fused below)

| Compound No. | $R^1$ | X | Y | $R^2$ | $R^3$ | Boiling point (b.p.) or melting point (°C.)/ or refractive index ($n_D^{20}$) |
|---|---|---|---|---|---|---|
| 35 | $(CH_3)_3C-$ | CO | CH | \multicolumn{2}{c}{$-CH_2-CH_2-$} | 188 |
| 36 | $(CH_3)_3C-$ | CO | CH | $-CH_2-C\equiv CH$ | $-CH_2-C\equiv CH$ | viscous oil |
| 37 | $(CH_3)_3C-$ | CO | CH | $-CH_2-CH=CH_2$ | $-CH_2-CH=CH_2$ | $n_D^{20} = 1.5600$ |
| 38 | $(CH_3)_3C-$ | CO | CH | $-CH_2-C_6H_5$ | $-CH_2-C_6H_5$ | 85 |
| 39 | $(CH_3)_3C-$ | CO | CH | $-CH_2-C_6H_4Cl$ (o) | $-CH_2-C_6H_4Cl$ (o) | 107 |
| 40 | $C_6H_5$ | CO | CH | $-CH_2-C_6H_4-Cl$ (p) | $-CH_2-C_6H_4-Cl$ (p) | viscous oil |
| 41 | $(CH_3)_3C-$ | CO | CH | \multicolumn{2}{c}{$-CH_2-$} | 194–96 |
| 42 | $(CH_3)_3C-$ | CO | CH | $-CH(CH_3)_2$ | $-CH(CH_3)_2$ | 61 |
| 43 | $C_6H_5$ | CO | CH | $-CH_2-C\equiv CH$ | $-CH_2-C\equiv CH$ | resin |
| 44 | $(CH_3)_3C-$ | CH(OH) | CH | $-CH_2-C_6H_4-Cl$ | $-CH_2-C_6H_4-Cl$ | 165 |
| 45 | $(CH_3)_3C-$ | CH(OH) | CH | \multicolumn{2}{c}{$-CH_2-CH_2-$} | 145 |
| 46 | $C_6H_5$ | CH(OH) | CH | $-CH_2-C_6H_4-Cl$ | $-CH_2-C_6H_4-Cl$ | 164–65 |
| 47 | $(CH_3)_3C-$ | CH(OH) | CH | $-CH_3$ | $-CH_3$ | 78–83 |
| 48 | $(CH_3)_3C-$ | CH(OH) | CH | $-CH_2-CH=CH_2$ | $-CH_2-CH=CH_2$ | 113 |
| 49 | $(CH_3)_3C-$ | CH(OH) | CH | $-CH_2-C_6H_4Cl$ (o) | $-CH_2-C_6H_4Cl$ (o) | 177 |
| 50 | $(CH_3)_3C-$ | CH(OH) | CH | \multicolumn{2}{c}{$-CH_2-$} | 149–51 |
| 51 | $(CH_3)_3C-$ | CH(OH) | CH | $-CH(CH_3)_2$ | $-CH(CH_3)_2$ | 129–31 |
| 52 | $(CH_3)_3C-$ | CO | N | \multicolumn{2}{c}{$-CH=CH-$} | 130–32 |
| 52 | cyclohexyl-CH$_3$ | CO | CH | \multicolumn{2}{c}{$-CH_2-$} | 184–85 |
| 54 | $(CH_3)_3C-$ | CH(OH) | N | \multicolumn{2}{c}{$-CH=CH-$} | 104–06 |
| 55 | cyclohexyl-CH$_3$ | CH(OH) | CH | \multicolumn{2}{c}{$-CH_2-$} | 138–40 |

The fungicidal activity of the compounds of this invention is illustrated by the following biotest examples.

In these examples, the compounds according to the present invention are each identified by the number (given in brackets) from Examples 1 to 3 and Table 1.

The known comparison compounds are identified as follows:

(A) = (CH$_3$)$_3$C—CO—C=CH—[naphthyl]
          |
          N
         / \
        ‖   N
        N——‖

(B) = (CH$_3$)$_3$C—CH(OH)—C=CH—[naphthyl]
              |
              N
             / \
            ‖   N
            N——‖

Example 4

Erysiphe test (barley)/protective

Solvent: 100 parts by weight of dimethylformamide
Emulsifier: 0.25 parts by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dew-moist. After the spray coating had dried on, the plants were dusted with spores of *Erysiphe graminis* f. sp. hordei.

The plants were placed in a greenhouse at a temperature of about 20° C. and a relative atmospheric humidity of about 80%, in order to promote the development of powdery mildew pustules.

Evaluation was carried out 7 days after the inoculation.

In this test, a clearly superior activity compared with the prior art was shown, for example, by the compounds (38), (7), (8), (42), (19), (22), (45), (51), (2), (47), (28), (48), (25), (32), (27), (29) and (30).

Example 5

Erysiphe test (barley)/seed treatment

The active compounds were used as dry dressings. These were prepared by extending the particular active compound with a ground mineral to give a finely pulverulent mixture, which ensured uniform distribution on the seed surface.

To apply the dressing, the seed was shaken with the dressing in a closed glass flask for 3 minutes.

3 batches of 12 grains of the barley were sown 2 cm deep in standard soil. 7 days after sowing, when the young plants had unfolded their first leaf, they were dusted with spores of *Erysiphe graminis* f. sp. hordei.

The plants were placed in a greenhouse at a temperature of about 20° C. and a relative atmospheric humidity of about 80% in order to promote the development of powdery mildew pustules.

Evaluation was carried out 7 days after the inoculation.

In this test, a clearly superior activity compared with the prior art was shown, for example, by the compounds (2), (47) and (29).

It is understood that the specification and examples are illustrative but not limitative of the present invention and that other embodiments within the spirit and scope of the invention will suggest themselves to those skilled in the art.

We claim:

1. An azolylvinyldithioacetal of the formula $$R^1-X-C=C\begin{matrix}SR^2\\SR^3\end{matrix}$$
with N—Y azole ring attached in which R$^1$ is an alkyl group having 1 to 4 carbon atoms, a cycloalkyl group having 3 to 7 carbon atoms and optionally substituted by alkyl having 1 to 4 carbon atoms, an alkoxy group having 1 to 4 carbon atoms or a phenyl group optionally substituted with at least one substituent selected from halogen, alkyl, alkoxy and alkylthio each having 1 to 4 carbon atoms, halogenoalkyl, halogenoalkylthio each having 1 or 2 carbon atoms and up to 5 identical or different halogen atoms and phenoxy and phenyl optionally substituted by halogen and/or by alkyl having 1 or 2 carbon atoms; and R$^2$ and R$^3$ both are an alkyl group having 1 to 4 carbon atoms; an alkenyl or alkinyl group each having 2 to 6 carbon atoms; a benzyl group optionally substituted on the phenyl ring by at least one of halogen, alkyl, alkoxy and alkylthio each having 1 to 4 carbon atoms, halogenoalkyl, halogenoalkoxy and halogenoalkylthio each having 1 or 2 carbon atoms and up to 5 identical or different halogen atoms, and phenoxy and phenyl optionally substituted by halogen and/or by alkyl having 1 or 2 carbon atoms; or a trialkylsilyl group having 1 to 4 carbon atoms in each alkyl part; or R$^2$ and R$^3$ together form an alkylene chain having 1 to 4 carbon atoms, a dialkylsilyl bridge having 1 to 4 carbon atoms in each alkyl part, or a —CH=CH— group, X is a keto group or a CH—(OH) group, and Y is a nitrogen atom or a CH group, or an addition product thereof with an acid or metal salt.

2. A compound according to claim 1, in which

R$^1$ is a tert.-butyl or isopropyl group, a cyclopropyl, cyclopentyl or cyclohexyl group which is optionally substituted by methyl, ethyl or propyl, a methoxy, ethoxy or butoxy group, a phenyl group optionally substituted by at least one of fluorine, chlorine, methyl, isopropyl, tert.-butyl, methoxy, methylthio, isopropoxy, trifluoromethyl, trifluoromethoxy, trifluoromethylthio, and phenoxy or phenyl which is optionally substituted by fluorine, chlorine and/or methyl; and R$^2$ and R$^3$ are identical and each is an alkyl group having 1 to 4 carbon atoms, an allyl or propargyl group or a benzyl group optionally substituted on the phenyl ring by at least one of fluorine, chlorine, methyl, isopropyl, tert.-butyl, methoxy, methylthio, isopropoxy, trifluoromethyl, trifluoromethoxy, trifluoromethylthio, and phenoxy or phenyl which is optionally substituted by fluorine, chlorine and/or methyl, or R$^2$ and R$^3$ are identical and form a trimethylsilyl group, or $R^2$ and $R^3$ together form a methylene radical, a dimethylene or trimethylene chain, a dimethylsilyl bridge or a —CH=CH— group.

3. A compound according to claim 1, wherein such compound is 2,2-dimethyl-5,5-dibenzylthio-4-(1,2,4-triazol-1-yl)-pent-4-en-3-one of the formula

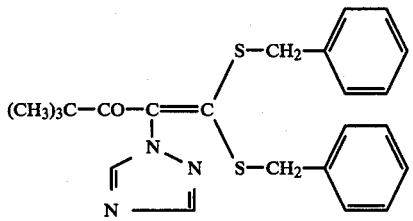

or an addition product thereof with an acid or metal salt.

4. A compound according to claim 1, wherein such compound is 1-phenyl-2-(1,2,4-triazol-1-yl)-2-(1,3-dithiolan-2-ylidene)-ethanol of the formula

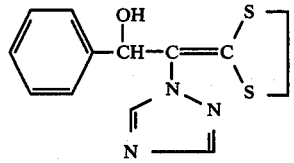

or an addition product thereof with an acid or metal salt.

5. A compound according to claim 1, wherein such compound is 2,2-dimethyl-5,5-dimethylthio-4-(imidazol-1-yl)-pent-4-en-3-ol of the formula

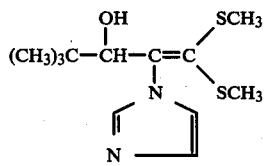

or an addition product thereof with an acid or metal salt.

6. A compound according to claim 1, wherein such compound is 2,2-dimethyl-5,5-diallylthio-4-(imidazol-1-yl)-pent-4-en-3-ol of the formula

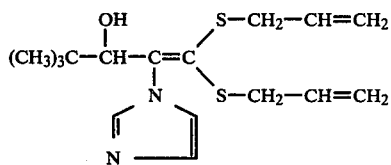

or an addition product thereof with an acid or metal salt.

7. A compound according to claim 1, wherein such compound is 2,2-dimethyl-5,5-diisopropylthio-4-(imidazol-1-yl)-pent-4-en-3-ol of the formula

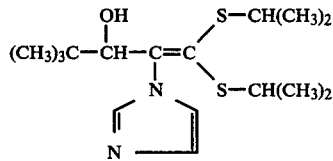

or an addition product thereof with an acid or metal salt.

8. A fungicidal composition comprising a fungicidally effective amount of a compound according to claim 1 in admixture with a diluent.

9. A method of combating fungi comprising applying to the fungi, or to a habitat thereof, a fungicidally effective amount of a compound according to claim 1.

10. The method according to claim 9, wherein such compound is
2,2-dimethyl-5,5-dibenzylthio-4-(1,2,4-triazol-1-yl)-pent-4-en-3-one,
1-phenyl-2-(1,2,4-triazol-1-yl)-2-(1,3-dithiolan-2-ylidene)-ethanol,
2,2-dimethyl-5,5-dimethylthio-4-(imidazol-1-yl)-pent-4-en-3-ol,
2,2-dimethyl-5,5-diallylthio-4-(imidazol-1-yl)-pent-4-en-3-ol or
2,2-dimethyl-5,5-diisopropylthio-4-(imidazol-1-yl)-pent-4-en-3-ol,
or an addition product thereof with an acid or metal salt.

* * * * *